United States Patent [19]

Drewlow

[11] Patent Number: Plant 7,292

[45] Date of Patent: Aug. 7, 1990

[54] KALANCHOE PLANT NAMED SOMBRERO

[75] Inventor: Lyndon W. Drewlow, Ashtabula, Ohio

[73] Assignee: Mikkelsens, Inc., Ashtabula, Ohio

[21] Appl. No.: 318,180

[22] Filed: Mar. 2, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 4,817 1/1982 Bürki ..... Plt. 68
P.P. 5,347 11/1984 Sommer ..... Plt. 68
P.P. 5,348 11/1984 Finger ..... Plt. 68
P.P. 5,387 1/1985 Hope ..... Plt. 68
P.P. 5,875 2/1987 Mikkelsen ..... Plt. 68
P.P. 5,961 4/1987 Mikkelsen ..... Plt. 68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Sombrero specifically developed for its ability to produce cut flowers. Sombrero has tall, upright stems that carry orange flowers, excellent lateral branching, large leaves, open inflorescence, and long lasting flowers that do not fade under high temperatures or as flowers age and which remain open under low light conditions.

1 Drawing Sheet

The present invention relates to a new and distinctive cultivar of Kalanchoe plant, botanically known as *Kalanchoe blossfeldiana*, and known by the cultivar name Sombrero. The new cultivar was developed by me through controlled breeding by crossing Mikkelsen Seedling No. 83-2291-2 (seed parent) with Mikkelsen Seedling No. 83-2293-2 (pollen parent). A principal objective of the breeding program was to develop Kalanchoe cultivars having certain desired characteristics and which could be used to produce cut flowers.

Asexual reproduction of stem cuttings has shown that the unique features of this new kalanchoe are stabilized and are reproduced true to type in successive propagations.

The following characteristics distinguish the new Kalanchoe from both its parent cultivars and other cultivated Kalanchoes of this type known and used in the floriculture industry. In order to describe the characteristics more meaningfully, references are made to known pot type kalanchoe cultivars, including Flamboyant (U.S. Plant Pat. No. 5,875), Tropicana (U.S. Plant Pat. No. 5,961), and Bali (U.S. Plant Pat. No. 5,348). Also referred to are Desert Blaze, Passionate, Lemon Drop and Bashful, all cut flower type cultivars of applicant disclosed in pending plant applications.

1. Sombrero is an upright, tall cut flower type kalanchoe characterized by orange flowers deeper in color than the pot type cultivar Flamboyant, but not as deep orange as the pot types Tropicana and Bali.

2. Sombrero is much taller than Tropicana, Bali and Flamboyant, slightly taller than Passionate but not as tall as Desert Blaze, Bashful, and Lemon Drop.

3. Sombrero has generally ten lateral branches which is similar to Bashful and Passionate, while Lemon Drop and Passionate generally have eight lateral branches. The three pot type cultivars will generally have eight to ten lateral branches.

4. Flower size of Sombrero is larger than Tropicana, Bali and Passionate, similar to Flamboyant, Desert Blaze and Lemon Drop, but not as large as Bashful.

5. Leaves of Sombrero are larger than any of the other comparison cultivars.

6. Mature stigmatic surfaces of Sombrero are whitish as are Flamboyant, Tropicana, Bali, and Lemon Drop, while Bashful, Passionate and Desert Blaze have a reddish pink cast especially near the center of the four stigmas.

7. Leaf margins are large lobed and shallow cut, similar to Flamboyant and Lemon Drop. All other comparison cultivars have finely lobed deeper cut serrations.

8. Leaf color is a lighter green similar to Lemon Drop and Flamboyant, with all other comparisons being darker green and Tropicana and Bashful the darkest green.

9. The five cut flower type kalanchoes tend to have very little basal branching from the lower two nodes, while the pot plant type comparison cultivars tend to break from all nodes.

10. The inflorescence of Sombrero and the other four cut flower types are open with flowers carried at the ends of long branches, while the pot plant types have dense compact inflorescence with flowers on the end of short branches producing a mass of color.

11. Long lasting flowers that do not fade easily under high temperatures or as the flower ages.

12. Strong, upright stems.

13. Flowers remain open under low light conditions after one dark to light conditioning cycle after cutting.

14. Can be grown on a schedule to provide cut flowers every week of the year.

The accompanying colored photograph is a top perspective view, illustrating the overall appearance of Sombrero and showing color as true as it is reasonably possible to obtain in a colored reproduction of this type. The photograph was taken in late June 1988.

The following is a detailed description of my new Kalanchoe cultivar based on plants produced under commercial practices in Ashtabula, Ohio, under greenhouse conditions. The description is based on plant cuttings five (5) weeks old stuck in six (6) inch pots and given two (2) weeks of long days and then short days to induce flowering. The plants were grown at 64°-68° F. night temperatures. Measurements were taken twelve (12) weeks after the start of short days, with plant height being measured from the soil line of the pot. Growth regulators were not used either on Sombrero or the comparison cultivars referred to. Color references are made to The Royal Horticultural Society Colour Chart except where general color terms of ordinary dictionary significance are used.

Parentage: A controlled cross between female parent Mikkelsen Seedling 83-2291-2 and male parent Mikkelsen Seedling 83-2293-2.

Propagation:

(A) *Type cutting.*—Stem tip cutting up to 3 cm long.

(B) *Time to root.*—10 days at 21° C. summer; 14 days at 21° C. winter.

(C) *Rooting habit.*—Abundant, fine, fibrous.

Plant description:

(A) *Form.*—Tall, upright, flower clusters (inflorescence) are carried on long strong stems above the main leaf mass; larger leaves are at base and middle of plant with only small leaves in the flower cluster.

(B) *Habit of growth.*—Upright, branching generally occurs from all nodes except the basal; occasionally one may form from the basal node. Spray type flower cluster is formed. Sombrero is 43–47 cm tall based on growing conditions described above. Environment will play a role in final height of plant.

(C) *Foliage.*—Leaves simple and opposite. (1) Size: Average full grown leaf is 17 to 18 cm long and 9 to 10 cm wide from a plant grown in a 15 cm pot. Growth conditions will cause leaf size to vary. (2) Shape: Ovate; apex obtuse; base is rounded. (3) Texture: Glabrous, corlaceous and succulent. (4) Margin: Crenate to dentate (in general smaller leaves in flower cluster). (5) Color: Young foliage, top side between 146A and 147A; Young foliage, under side near 147B; Mature foliage, top side near 147A; Mature foliage, under side near 147B.

Flowering description:

(A) *Flowering habits.*—Inflorescence is a cyme. Terminal flower on main axis opens first followed by the terminal flowers of the lateral branches, continuing with subsequent development of branches in the inflorescence. Inflorescence is made up of main stem and up to ten lateral branches. The inflorescence is approximately 33–36 cm in height and 18–20 cm in diameter. The inflorescence is more open as opposed to the shorter, more dense and compact inflorescence habit of the pot type cultivars.

(B) *Natural flowering season.*—Early January. Flowering time under controlled daylength at 20° C. in summer is nine weeks; in winter is twelve weeks. Flowering time depends on temperature, light intensity and other growing conditions. In general, higher temperatures (to the point of heat delay) and increased light intensity will speed up flowering, and low temperatures and light intensity will delay flowering. Other conditions that can cause delay in flowering are low fertility, very high night temperatures (80° F. plus) and moisture stress.

(C) *Flower buds.*—Oblong, up to 10 mm long just before showing first color, developing tubular as flower petals mature. Sheath with four green sepals.

(D) *Flowers borne.*—Compound dichasial cymes, primary peduncle 11 mm in diameter just below the first branch of the inflorescence; length of peduncle will vary depending on cultural conditions. In general, peduncles will be shorter when plants are moisture stressed, grown well spaced, grown under high light intensity, grown under low temperatures, or are given applications of growth regulators. If plants are grown crowded and/or under low light conditions, the peduncles will tend to stretch badly. Pedicels vary in length depending on where they are located in the inflorescence. The pedicels become shorter the higher they are in the inflorescence, that is, the closer they are to the apical meristem.

(E) *Quantity of flowers.*—Very floriferous, with more than 100 flowers on the main axis and 50 or more flowers on the side branches. Inflorescence is indeterminant in nature.

(F) *Petals.*—(1) Shape and size: Almost rounded, top cuspidate. Each petal is approximately 8 mm long and 6 mm wide, with the diameter of an individual flower being approximately 16 mm. (2) Color: top side when opening between 33A and 33B, fading to between 32B and 32C; under side 32D. (3) Number of Petals: 4.

(G) *Reproductive organs.*—(1) Number of Stamens: Eight. (a) Anther shape: Flat elliptical; color — yellowish green. (b) Filament color: Whitish green. (c) Pollen color: Yellow. (2) Pistils: (a) Stigma shape: Flat; color — light green. (b) Style color: Whitish. (c) Ovaries: Number — 4; size — 7 mm; color — green.

Disease resistance: Sombrero has shown good resistance to powdery mildew.

I claim:

1. A new and distinct cultivar of Kalanchoe plant named Sombrero, as illustrated and described.

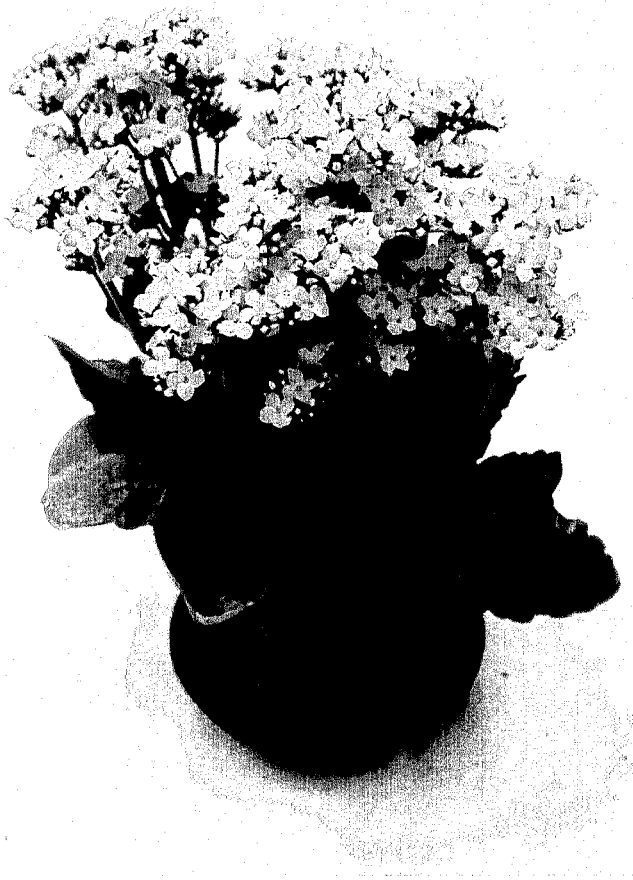

* * * * *